United States Patent [19]
Rechsteiner et al.

[11] Patent Number: 5,763,225
[45] Date of Patent: *Jun. 9, 1998

[54] SYNTHESIS OF PEPTIDES AS CLONED UBIQUITIN EXTENSIONS

[75] Inventors: Martin C. Rechsteiner; Yung Yoo, both of Salt lake City, Utah; Kevin V. Rote, Lake Villa, Ill.

[73] Assignee: The University of Utah, Salt Lake City, Utah

[*] Notice: The term of this patent shall not extend beyond the expiration date of Pat. No. 5,620,923.

[21] Appl. No.: 555,579

[22] Filed: Nov. 8, 1995

Related U.S. Application Data

[60] Continuation of Ser. No. 862,737, Apr. 3, 1992, Pat. No. 5,620,923, which is a division of Ser. No. 420,544, Oct. 12, 1989, abandoned.

[51] Int. Cl.$^6$ .................................................. C12N 15/62
[52] U.S. Cl. .................... 435/69.7; 435/69.1; 435/172.3; 435/252.3; 435/320.1; 530/412; 530/324; 530/350
[58] Field of Search .................................. 435/69.7, 69.1, 435/172.3, 252.3, 320.1; 530/412, 324, 350; 536/23.4

[56] References Cited

U.S. PATENT DOCUMENTS

| | | | |
|---|---|---|---|
| 5,093,242 | 3/1992 | Bachmair | 435/69.7 |
| 5,132,213 | 7/1992 | Bachmair | 435/69.7 |
| 5,156,968 | 10/1992 | Liu | 435/224 |

FOREIGN PATENT DOCUMENTS

| | | |
|---|---|---|
| 8403103 | 8/1984 | WIPO . |
| WO 88/02406 | 4/1988 | WIPO . |
| WO 89/12678 | 12/1989 | WIPO . |

OTHER PUBLICATIONS

Yoo and Rechsteiner, *Anal.Biochem.,* 191:35–40, 1990.
Wilkinson, *Methods in Enzymology,* 185:387–397,1990.
Lowe, et al., Ubiquitin Carboxyl–Terminal Hydrolase (PGP 9.5) is Selectively Present in Ubiquitinated Inclusion Bodies Characteristic of Human Degenerative Diseases, *J. Pathol.* 161:153–160, 1990.
Mayer et al., Abstract from the Second International Conference on Alzheimer's Disease and Related Disorder, Toronto, Canada, 15–20 Jul., 1990.
Wilkinson, et al., Abstract from the ASBMB/AAI Meeting, 1990.
Liu et al., *J. Biol. Chem.* 264(34):20331–20338, 1989.
Wilkinson, et al., The Neuron–Specific Protein PGP 9.5 Is a Ubiquitin Carboxyl–Terminal Hydrolase, *Science,* 246:670–673, 1989.
Yoo, et al., *J. Biol. Chem.,* 264(29):17078–17083, 1989.
Miller, et al., *Bio/Technology,* 7:698–704, 1989.
Jonnalagadds, *J.Biol. Chem.,* 264(18):10637–10642, 1989.
Ecker, et al., *J. Biol. Chem.,* 264(13):7715–7719, 1989.
Monia, *J. Biol. Chem.,* 264(7):4093–4103,1989.

Mayer & Wilkinson, Detection, Resolution, and Nomenclature of Multiple Ubiquitin Carboyyl–Terminal Esterases from Bovine Calf Thymus, *Biochemistry,* 28:166–172, 1989.
Duerksen–Hughes, Affinity Chromatography Using Protein Immobilized via Arginine Residues, *Biochemistry,* 28:8530–8536, 1989.
Wilkinson, Ubiquitin, Ed. M. Rechsteiner, Plenum Publishing corporaiton, 1988, pp. 5–38.
Booth, et al., *J. Biol.Chem.,* 263(31):16364–16371, 1988.
Ecker, et al., *J. Biol.Chem.,* 262(29):14213–14221, 1987.
Ecker, et al., *J. Biol.Chem.,* 262(8):3524–3527, 1987.
Wilkinson, Protein Ubiquitination: a regulatory post–translational modification, *Anti–Cancer Drug Design,* 2:211–229, 1987.
Duerksen–Hughes, *Biochemistry,* 26:6980–6987, 1987.
Bachmair, et al., In Vitro Half Life of Protein is a Function of its Amino Terminal Residue, *Science,* 234:179–186, 1986.
Wilkinson, et al., Synthesis and Characterization of Ubiquitin Carboxyl–Terminal Hydrolase, *Biochemistry,* 25:6644–6649, 1986.
Wilkinson, et al., Synthesis and Characterizaiton of the Carboxyl–Terminal Ethyl Ester of Ubiquitin, Abstracts from the ASBC/DBC, ACS meeting, 14 Jan., 1986.
PTO Manual of Patent Classification, 530–1—530–3, Dec. 1990.
Butt et al., "Ubiquitin Fusion Augments the Yield of Cloned Gene Products in *Escherichia coli,*" *PNAS USA,* 86:2540–2544 (1989).
Pickart and Rose, Ubiquitin Carboxyl–Terminal Hydrolase Acts on Ubiquitin Carboxyl–Terminal Amides, *J. Biol. Chem.* 260:7903–7910 (1985).

(List continued on next page.)

*Primary Examiner*—Stephen Walsh
*Assistant Examiner*—Eliane Lazar-Wesley
*Attorney, Agent, or Firm*—Arnold, White & Durkee

[57] ABSTRACT

A method for the preparation of synthetic peptide products containing up to about forty amino acid residues as ubiquitin-carboxyl terminal extensions expressed in procaryotic cells such as *E. coli* is disclosed. This is accomplished by cloning appropriate oligonucleotides encoding the desired peptide as a ubiquitin peptide extension gene, splicing the gene into an appropriate plasmid which, in turn is transformed into *E. coli,* or other appropriate procaryotic cells and inducing expression of the ubiquitin peptide fusion product. When expressed, the cells produce recoverable amounts of ubiquitin extended at its carboxyl terminus by the encoded carboxyl terminal extended peptide (CTEP). The peptide can be recovered as ubiquitin fused extension products (Ub-CTEP) or, alternatively, can be cleaved from the ubiquitin by an appropriate eucaryotic peptidase and purified. The process is adaptable to the production of any desirable peptide containing from 2 to about 40 amino acid residues and is particularly adaptable to the production of peptides containing between about 5 and 40 amino acid residues.

5 Claims, 2 Drawing Sheets

OTHER PUBLICATIONS

Cox, et al., Tryptic Peptide Mapping of Ubiquitin and Derivatives Using Reverse Phase HPLC, *Analytical Biochemistry*, 154: 345–352, (1986).

Creighton, T.E., ed *Proteins, Structures and Molecular Properties*, WH Freeman and Co., New York, 1993, pp.466–468.

Kane and Hartley, Formation of Recombinant Protein Inclusion Bodies in *Escherichia coli, Trends, Biotechnol.* 6:95–101 (1988).

Rechsteiner, et al., Protein Structure and Instracellular Stability, *TIBS* 12:390–394 (1987).

Butt, et al., Ubiquitin–Metallothionein Fusion Protein Expression in Yeart, J. Biol. Chem. 263:16364–16371 (1988).

Wilkinson, et al., Comparisons of neuronal (PGP 9.5) and non–neuronal ubiquitin C–terminal hydrolases, *Biochemical Sociey Transactions* 20:631–637 (1992).

Mayer, Master's Thesis, Emory University, 1986.

Rose and warms, An Enzyme with UIbiuitin Carboxy–Terminal Esterase Activity from Reticulocytes, Biochemistry 22:4234–4257 (1983).

Ozkaynak et al., "The Yeast Ubiauitin Gene: A Family of Natural Gene Fusions," *EMBO J*, 6:1429–1439, May 1987.

Jonnalagadda et al., "Expression and Accurate Processing of Yeast Penta–ubiquitin in *Escherihia coli,*" *Journal of Biological Chemistry*, 262(36):17750–17756. 1987.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Met  Glu  Phe  Met  His  Ile  Ser  Pro  Pro  Glu  Pro  Glu  Ser  Glu  Glu  Glu
1              5                        10                       15
Glu  Glu  His  Ser  Ser
               20
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met  Glu  Phe  Met  His  Glu  Ser  His  Ser  Ser
1              5                        10
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

```
Met  Glu  Phe  Met  His  Ile  Ser  Pro  Pro  Glu  Pro  Glu  Ser  His  Ser  Ser
1              5                        10                       15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

```
Met  Glu  Phe  Met  His  Glu  Ser  Glu  Glu  Glu  Glu  Glu  His  Ser  Ser
1              5                        10                       15
```

SYNTHESIS OF PEPTIDES AS CLONED UBIQUITIN EXTENSIONS

This is a continuation of application Ser. No. 07/862,737, filed Apr. 3, 1992, now U.S. Pat. No. 5,620,923 which was a divisional of Ser. No. 07/420,544, filed Oct. 12, 1989, now abandoned.

The government owns certain rights in the present invention pursuant to NIH grant GM37009.

This invention relates to the synthesis of peptides as ubiquitin extensions cloned in *E. coli*. More particularly, this invention relates to the synthesis of peptides containing up to about 40 amino acid residues as ubiquitin carboxyl extension products cloned from synthetic genes and expressed in *E. coli*.

BACKGROUND OF THE INVENTION AND DISCUSSION OF PRIOR ART

Synthetic peptides are valuable research tools in a variety of biological disciplines. Small peptides are widely used to generate antibodies. Immunologists have found peptides useful for assessing antigenic variation and for studying antigen presentation. Cell biologists employ small peptides to disrupt cell-substrate adhesion and to target proteins to specific cellular compartments. Peptides have long served as model systems in studies on the structure, folding or associations of proteins. Peptides also possess useful therapeutical or pharmacological properties.

Obtaining small peptides using solid phase synthetic techniques is a lengthy, laborious and expensive process. A recent survey showed the average cost for a 25-residue peptide to be in excess of $2,000. In solid phase synthesis, the peptide must be built one residue at a time, with changes of chemicals between each coupling step. Moreover, repetitive couplings become increasingly necessary as the peptide chain lengthens. Purification of the desired synthetic peptide from among truncated or otherwise aberrant synthetic peptides can also prove very troublesome.

The expression of ubiquitin fusion proteins in *E. coli* and the subsequent purification are described by Monia et al. J. Biol. Chem. 264, 4093–4103 (Mar. 5, 1989). These carboxyl extension proteins (CEP) are from 52 to 80 amino acids in length and are naturally occurring proteins found in various organisms ranging from yeast to humans.

Ecker et al. J. Biol. Chem. 264, 7715–7719 (May 5, 1989) teach the expression of cloned eucaryotic genes in microorganisms to allow for the isolation of large quantities of naturally occurring protein products which are present in only trace amounts from natural sources. However, Ecker et al. state that expression of these genes in *E. coli* often leads to gene products which do not fold properly and are not biologically active. Instead, *Saccharomyces cerevisiae* is stated to be a superior expression host. Protein yield is stated to increase when genes are expressed in yeast by fusion to ubiquitin. The proteins produced in this manner are the subunit of the mammalian stimulating G-protein of the adenylate cyclase complex; a soluble fragment of the T cell receptor protein; and the protease domain of human urokinase.

Butt et al., Proc. Natl. Acad. Sci. 86, 2540–2544 (April 1989) teach an expression system for cloning ubiquitin-fusion proteins using *E. coli* and state that fusion of ubiquitin by its carboxyl terminal end to the N-terminus of these proteins increases the yield of unstable or poorly expressed proteins such as those referred to by Ecker et al, supra. Butt et al. conclude that ubiquitin fusion technology has the potential for general application in augmenting the yield of cloned gene products in both procaryotes and eucaryotes.

As early as 1986, Bachmair et al., Science 234, 179–186 (1986), suggest that ubiquitin may be helpful in preparing [beta]-galactosidase fusion proteins having any N-terminal amino acid when expressed in both bacteria and yeast. When expressed in *Saccharomyces cerevisiae* cells, rapid cleavage of ubiquitin from the [beta]-galactosidase occurred with any amino acid except proline. When expressed in *E. coli*, the fusion proteins were not disassembled.

One disadvantage of expressing ubiquitin fusion proteins in eucaryotic cells is that they contain hydrolases, i.e. peptidases, as natural products which break the junction of the ubiquitin-fusion protein and, in many cases, target the fusion protein for proteolytic degradation after removing ubiquitin. Bachmair et al., supra, do state that joining ubiquitin to the amino-terminus of target proteins, to yield linear ubiquitin fusion products may be feasible by constructing appropriate genes and expressing them in vivo.

In the prior art, the emphasis is on the use of both eucaryotic and procaryotic cell expressions utilizing ubiquitin fusion proteins for the cloning and production of natural intracellular proteins. These natural proteins are often larger than ubiquitin. Wilkinson et al., Arch. Biochem. Biophys. 250, 390–399 (1986), speculate that ubiquitin may undergo conformational changes following attachment to a target protein. It is possible that proteins having residues approaching or exceeding those of ubiquitin dominate, or at least interfere, with the favorable stability properties of the ubiquitin molecule rendering it less effective as a substrate for fusion protein synthesis.

OBJECTS AND BRIEF SUMMARY OF THE INVENTION

It is an object of the present invention to prepare synthetic ubiquitin peptide fusion products containing up to about forty additional amino acid residues as ubiquitin extensions expressed in procaryotic cells and in *E. coli* in particular.

It is also an object of this invention to obtain pure synthetic peptides, expressed in procaryotic cells as ubiquitin extensions, by cleavage of the peptide from ubiquitin by an appropriate hydrolase followed by purification of the peptide.

A further object of this invention is to obtain purified synthetic ubiquitin extension peptides as cloned products from procaryotic cells.

These and other objects may be accomplished by means of preparing appropriate oligonucleotides encoding the desired peptide as a ubiquitin peptide extension gene, splicing the gene into an appropriate plasmid which, in turn is transformed into *E. coli*, or other appropriate procaryotic cells capable of expressing the ubiquitin extension peptide. When expressed, the cells produce recoverable amounts of ubiquitin extended at its carboxyl terminus by the encoded peptide. The peptide can be recovered as ubiquitin peptide fusion products (sometimes referred to herein as Ub-carboxyl terminal extended peptide or Ub-CTEP) or, alternatively, can be cleaved from the ubiquitin by an appropriate eucaryotic hydrolase and purified. The process is adaptable to the production of any desirable peptide containing from 2 to about 40 amino acid residues and is particularly adaptable to the production of peptides containing between about 5 and 40 amino acid residues. When producing peptides of this size, the properties of ubiquitin should dominate the fusion product.

DETAILED DESCRIPTION OF THE INVENTION

Figure 1A:
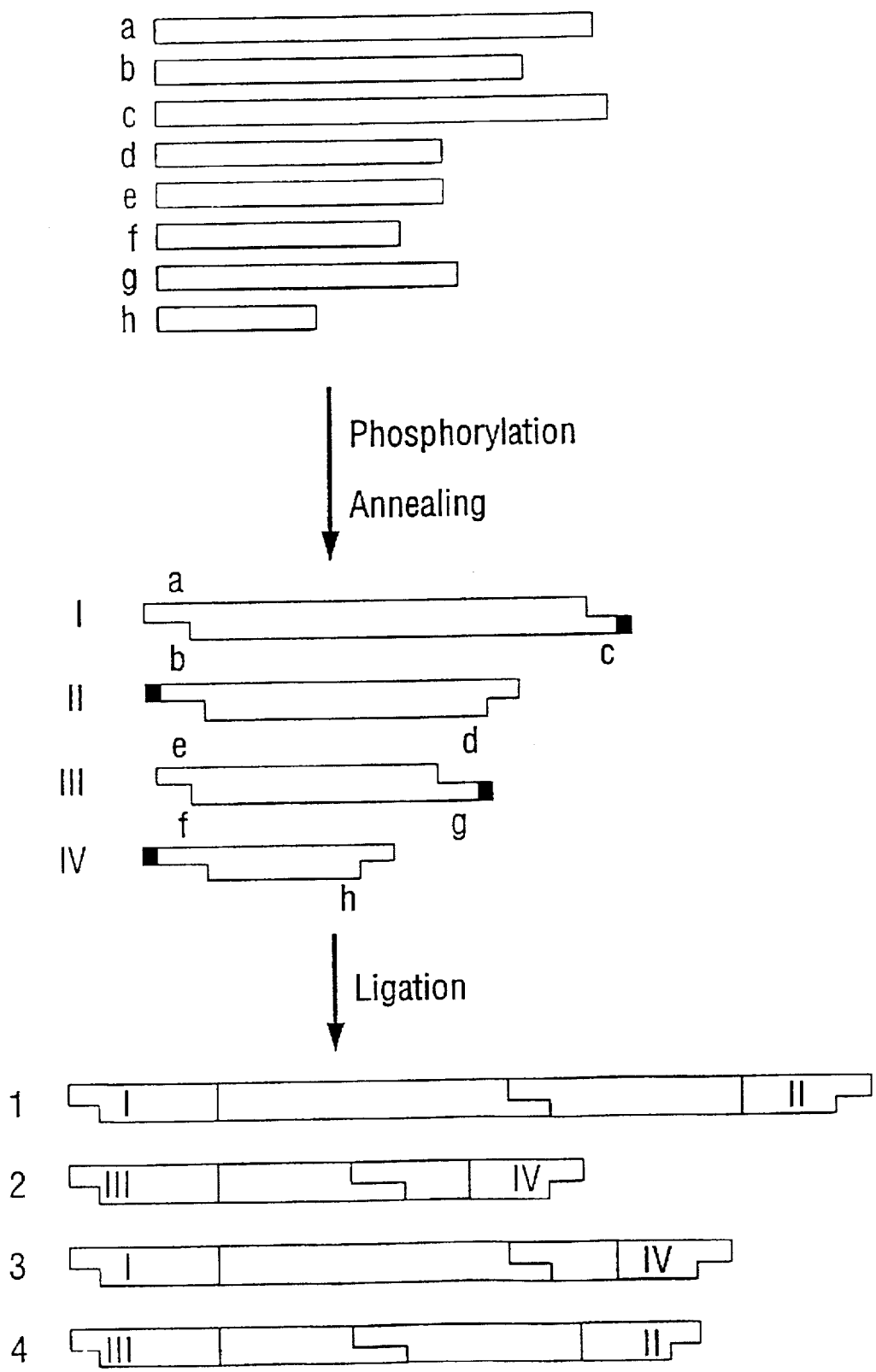
FIG. 1a is a schematic representation of preparation of appropriate oligonucleotides, phosphorylating and annealing the oligonucleotides into complimentary DNA segments and ligating these segments into longer DNA strands encoding the desired peptides which are to be prepared.

Ubiquitin is a highly conserved, 76-residue protein having a C-terminus composed of arg-gly-gly and is found in all eucaryotic cells both free and covalently conjugated to a variety of cellular proteins. Ubiquitin is found in cells as diverse as mammals, yeast and celery. Ubiquitin is attached by its carboxyl terminus to amino groups of other proteins. When ubiquitin is attached to the alpha-amino terminus, such products are referred to in the literature as ubiquitin carboxyl extension proteins. In eucaroytic cells, the extension proteins are cleaved from the ubiquitin molecule by hydrolases (peptidases). It has been postulated that attachment of ubiquitin to a protein is a signal for the latter's destruction by proteolysis. Ubiquitin is lacking in cysteine and tryptophan but there is nothing unusual about its sequence other than its extreme conservation. The identical sequences of animal ubiquitins differ only at three positions from the yeast and plant ubiquitin. The x-ray structure of ubiquitin, which has been resolved to 2.8 A, reveals a compact globular protein with the carboxyl terminal arg-gly-gly extended into the solvent. The molecule contains four strands of (beta)-sheet plus a single (alpha)-helix with three and one half turns; all sequence differences among species being located on a small portion of the ubiquitin surface. NMR studies have shown that ubiquitin remains folded at pHs of 1 to 13 and below 80° C. A distinct hydrophobic core and extensive hydrogen bonding are present, which may account for the molecule's exceptional stability. Ubiquitin has a neutral isoelectric point of 6.7 and a molecular weight of 8565.

Ubiquitin is extremely stable to heat and extremes of pH which are essential properties for its use as a substrate to facilitate preparation of peptides of the desired amino acid sequence and allow for cleavage therefrom by an appropriate enzyme.

For a detailed analysis of ubiquitin, its properties and functions, reference is made to the book "Ubiquitin", published by Plenum Press, N.Y. (1988) and edited by Martin Rechsteiner.

In the present invention it is desirable that the ubiquitin molecule remains in its native state such that the beneficial properties of ubiquitin as a substrate for carboxyl terminal extended peptide synthesis are unchanged. Therefore, the extended peptide should not be of a size that the properties of the peptide dominate the properties of the ubiquitin molecule. In order to accomplish this, the synthetic peptides prepared according to this invention will preferably be made up of between about 2 to 40 amino acid residues and will preferably be between about 5 and 40 amino acid residues.

By utilizing ubiquitin as a stable substrate in which to prepare carboxyl terminal extended peptides, it is possible to prepare any variety of peptides, having any desired amino acid sequence. The ubiquitin-peptide fusion product can be cleaved by appropriate cleavage enzymes which do not discriminate against any N-terminal amino acid of the peptide, with the possible exception of proline. Because cleavage of the peptide from the ubiquitin molecule consistently takes place between the C-terminal glycine and the N-terminal peptide amino acid, any variety of peptide can be repeatedly and consistently prepared by the methods described herein.

The eucaryotic enzymes that cleave peptides from the ubiquitin-peptide fusion products are necessary components in the production of pure peptides. Ubiquitin and the cleavage enzymes are either not present in procaryotes such as E. coli or are present in such small amounts as not to cleave the ubiquitin-extension peptide bond. Therefore, E. coli is used herein as the expression host since cleavage of ubiquitin extended at its carboxyl terminus by synthetic peptides will not occur without the addition of an appropriate cleavage enzyme. Moreover, E coli is an excellent host for gene expression because of its simplicity, the availability of strong regulatable promoters and high levels of expression of ubiquitin peptide fusion products. Rabbit reticulocytes are a rich source of ubiquitin-activating enzymes and proteases as described by Rechsteiner, Adv. Cell Biol. 3, 1–30 (1987) and Hershko, J. Biol. Chem. 263, 15237–15240 (1988). The nomenclature and mode of functioning of ubiquitin hydrolases are further described by Rose, "Ubiquitin Carboxyl-Terminal Hydrolases", at pp. 135–155 of Rechsteiner, Ubiquitin, supra. It is not known just how many ubiquitin carboxyl terminal hydrolases (UbCH), capable of liberating peptides from ubiquitin fusion proteins are present in eucaryotic cells. It is believed there are at least two. In the present invention two activities were found after fractionation of rabbit reticulocyte lysate on DEAE chromatography. Only one of these activities was partially purified and used. Likewise, Butt, et al., Proc. Natl. Acad. Sci. 86, 2540–2544 (April 1989) report two peaks of cleavage activity after DEAE chromatography. The specific enzyme to be used in cleaving the peptide from the ubiquitin is limited only by its functionality. In other words, the enzyme must be able to cleave the amide bond between the gly76 of ubiquitin and the N-terminal amino acid of the peptide. Further, the enzyme should not attack other amide bonds of ubiquitin or the extension peptide.

The preparation of an expression vector encoding the peptides to be produced as ubiquitin extensions may be accomplished either by constructing a synthetic oligonucleotide which encompasses the ubiquitin molecule plus the extension protein and splicing the same into an appropriate plasmid or by inserting oligonucleotides encoding the peptides to be produced into plasmid already containing a synthetic ubiquitin gene. The specific techniques may readily be determined by those having ordinary skill in the art. For purposes of illustrating the present invention a step by step procedure for the preparation of four different peptide sequences ranging from 10 to 21 residues will be described. These techniques, however, are illustrative only, and can be applied to the preparation of any number of synthetic peptides as ubiquitin extensions when incorporated into appropriate plasmids, which in turn are transformed into appropriate bacterial strains, such as E. coli, capable of expressing the DNA sequence. This is followed by recovery of the ubiquitin-carboxyl terminal extended peptide or, recovery of the peptide after cleavage from ubiquitin.

Construction of Expression Vectors

DNA duplexes encoding four different peptides were constructed from eight synthetic oligonucleotides, a through h, as graphically shown in FIG. 1a. The oligonucleotides were purified on 15% denaturing polyacrylamide gels, and oligonucleotides b, c, f and g were phosphorylated using T4 polynucleotide kinase. Complimentary segments a+c, b+d, e+g and f+h were annealed to form duplexes I, II, III and IV as shown in FIG. 1a. These complimentary strands were ethanol-precipitated and resuspended in ligation buffer containing 50 mM Tris, pH 7.4, 10 mM MgCl$_2$, 10 mM DTT, 1 mM spermidine, 1 mM ATP and 2 units of T4 ligase in a final volume of 25 ul and incubated at 16° C. for 16 hours to form longer duplexes encoding the four peptides. The reaction mixture was then extracted with phenol/chloroform, the DNA was precipitated with ethanol, dissolved in 20 ul of TE (10 mM Tris, 1 mM EDTA), pH 8.0 and the ligated duplexes, designated as 1, 2, 3 and 4 in FIG. 1a with the encoded peptides being shown by stippling, were purified on 12% non-denaturing acrylamide gels.

Figure 1B:
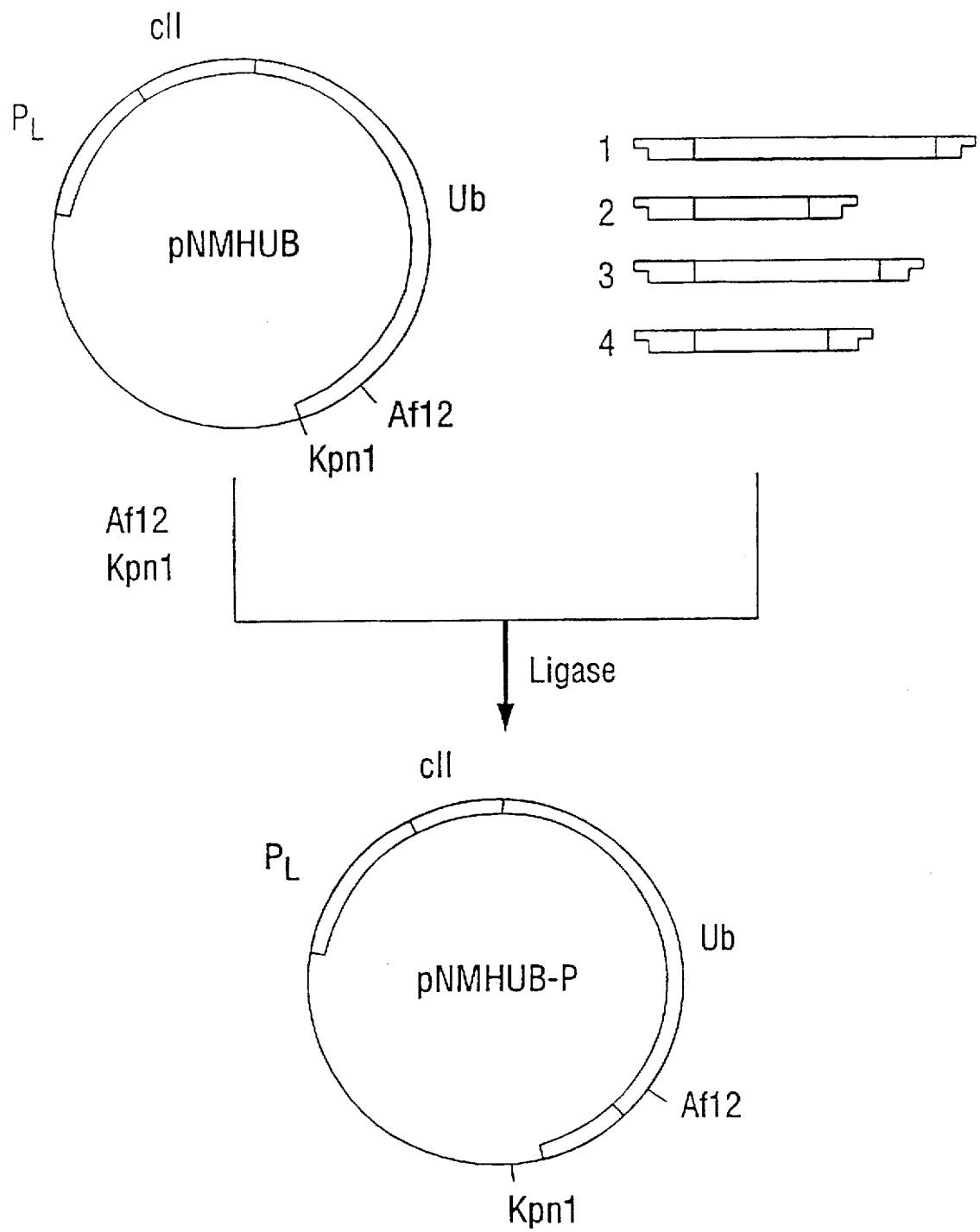
FIG. 1b is a map showing the incorporation of the DNA segments into a plasmid as an extension of a ubiquitin gene between restriction sites Afl2 and Kpnl to form an extended DNA segment encoding a ubiquitin-extension peptide.

Each synthetic gene thus prepared was cloned between the Afl2 and Kpn1 sites in the plasmid pNMHUB as illustrated in FIG. 1b to form the peptide encoded plasmid pNMHUB-P. Sites shown in FIG. 1b but not specifically referred to are readily understood by those skilled in the art and are not necessary to a complete understanding of the invention. The construction of plasmid pNMHUB, including the insertion of a synthetic human ubiquitin gene into a pMG27N-S plasmid is described by Ecker, et al., J. Biol. Chem., 262, 14213–14221 (1987). The synthetic ubiquitin gene is laced with convenient restriction sites. The C-terminus of the ubiquitin is bracketed by an Afl2 site at residue 70 and a Kpn1 site 5 bases beyond the termination codon as represented in FIG. 1b. Each construct was transformed into the wild-type lysogen, MM294CI$^+$. Transformants were identified by colony hybridization in the manner described by Maniatis, et al., Molecular Clonings, A Laboratory Manual, Cold Spring Harbor Laboratory, Cold Spring Harbor, N.Y. (1982), and positive transformants were confirmed by restriction enzyme analysis of isolated plasmids. The amino acid sequences of the four peptides encoded as ubiquitin extensions are as follows:

| Peptide No. | Amino Acid Sequence |
| --- | --- |
| 1 | MEFMHISPPEPESEEEEEHSS |
| 2 | MEFMHESHSS |
| 3 | MEFMHISPPEPESHSS |
| 4 | MEFMHESEEEEEHSS |

The standard one letter codes have been used to designate the amino acids where M is methionine, E is glutamic acid, F is phenylalanine, H is histidine, I is isoleucine, S is serine and P is proline.

Expression of Ubiquitin Extension Peptides

The plasmids containing genes for each peptide were separately expressed. The correct pNMHUB and pNMHUB-P plasmids were amplified, recovered and transformed into E. coli expression strain, AR13. Since the AR13 strain contains a temperature sensitive lambda repressor and the cloned genes are under the control of the lambda P$_L$ promoter, synthesis of ubiquitin peptide fusion products can be induced by heat. The transformed AR13 cells were grown to an OD$_{600}$=0.8 at 32° C. The temperature was rapidly shifted to 42° C. and after 3 hours the cells were harvested by centrifugation and disrupted by sonication. Both ubiquitin and ubiquitin-carboxyl terminal extended peptides accumulated in large amounts from expression in the AR13 cells. Densitometry of Coomassie blue stained gels showed that 3 hours after temperature shift, ubiquitin and ubiquitin-carboxyl terminal extended peptides represented approximately 15% of the total E. coli proteins. While heat induced expression is illustrated, the invention is not limited to this method only as any inducible promotor may be utilized.

Purification of Ubiquitin-Carboxyl Terminal Extended Peptides

In general, the ubiquitin-carboxyl terminal extended peptides may be purified in a three or four step procedure depending upon the purity obtained after the third step. Briefly, after expression, the cells are collected by centrifugation and disrupted by sonication. The resulting lysate is subjected first to heating, then to an ammonium sulfate step and finally to chromatography, such as DEAE-cellulose. If necessary, gel filtration, such as Sephadex G50, may be included to achieve full purification.

More specifically, the cells were harvested by centrifugation, resuspended in 50 mM Tris HCl, pH 7.4, 5% glycerol, 2 mM EDTA and 1 mM dithiothreitol, and disrupted by three one minute pulses using a Branson sonifier 450 at setting seven. The lysate was centrifuged at 10,000×g for 60 minutes and the supernate was collected, heated at 85° C. for 10 minutes and cooled on ice before centrifuging at 15,000×G for 45 minutes. The supernate was taken to 65% ammonium sulfate, clarified by centrifugation and the ubiquitin-carboxyl terminal extended peptides were collected in the 65–95% ammonium sulfate precipitate. After being dissolved in 50 mM Tris, pH 8.0 and dialyzed against the same buffer, they were filtered through a 0.22 um filter prior to adsorption on a 1×35 cm column of DEAE-cellulose in 50 mM Tris, pH 8.0. The ubiquitin-carboxyl terminal extended peptides were eluted from the column with 400 ml of a 0–0.3M linear gradient of NaCl. If necessary, fractions containing the ubiquitin-carboxyl terminal extended peptide proteins were pooled, concentrated by passage through an Amicon YM5 membrane and chromatographed on a 1.6×70 cm column of Sephadex G50 in 50 mM Tris, pH 8.0. Fractions containing pure ubiquitin-carboxyl terminal extended peptides were pooled, dialyzed against water and lyophilized.

It is difficult to calculate yields of the ubiquitin-peptide fusion products since they do not possess enzymatic activity. However, they constitute about 15% of the protein in the E. coli sonicate. A rough estimate of recovery was obtained as follows. Crude extracts from cells in 1 liter of medium contained 350–400 mg of protein of which about 75% was removed upon heating. Total protein in the 65–95% ammonia sulfate precipitate was 20–30 mg of which it was estimated that 90% was ubiquitin-carboxyl terminal extended peptide. DEAE cellulose and Sephadex G50 chromatography produced a final yield of 10–25 mg of pure ubiquitin-carboxyl terminal extended peptide. Thus, the purification procedure leads to the recovery of 10–25 mg from the 50–60 mg of ubiquitin-carboxyl terminal extended peptide present in the crude extract. The purified ubiquitin-carboxyl terminal extended peptides proteins are identified as Ub-CTEP1, Ub-CTEP2, Ub-CTEP3 and Ub-CTEP4 with numerals 1–4 referring to peptides 1–4 identified above.

Preparation of a Ubiquitin Carboxyl Terminal Hydrolase (UbCH)

UbCH was isolated from rabbit reticulocyte lysate using radioiodinated Ub-CTEP1 as substrate. The lysate was prepared as described by Hough et al., J. Biol Chem. 262, 8303–8311 (1987) and absorbed to a 1.6×64 cm column of Fractogel-TSK-DEAE 650S in 10 mM Tris, pH 7.0, 1 mM DTT and 20% glycerol (v/v). Fraction I (hemoglobin and ubiquitin) was eluted with 450 ml of the same buffer followed by 1200 ml of buffer [10 mM Tris HCl, pH 7.0, containing 25 mM KCl, 10 mM NaCl, 1.1 mM MgCl$_2$, 1 mM DTT, 0.1 mM EDTA and 20% glycerol]. The bound proteins were then eluted at 45 ml/hr with a 500 ml linear 0.1M –0.5M KCl gradient. UbCH activities eluted at two different salt concentrations. A portion of the major peak of activity was further purified by gel filtration on a Sephacryl S-200 column (1.6×90 cm) in buffer A. The active fractions of UbCH were concentrated using an Amicon PM10 membrane and used for cleaving the four Ub-CTEP extensions.

Cleavage of Extension Peptides from Ubiquitin

Peptides 1–4 were cleaved from ubiquitin using the partially purified UbCH enzyme described above. The enzyme fraction (100 ug of protein) was incubated with 100 ug of each of the purified ubiquitin-carboxyl terminal extended peptides described above in 100 ul of Tris HCl, pH 7.4 at 37° C. for 30 minutes. The reaction was stopped by heating at 85° C. for 5 minutes and the denatured proteins were removed by centrifugation at 15,000×g for 30 minutes. The supernate was analyzed by SDS-PAGE to assess the extent of the reaction. Specific cleavage at the carboxyl terminus of ubiquitin was verified by ubiquitin conjugation assays in HeLa extracts in the manner described by Carlson, et al., J. Cell Bio. 104, 537–546 (1987) using the processed ubiquitin. Except for the C-terminal arg-gly-gly residues that extend into the solvent, ubiquitin is a compact, relatively protease-resistant molecule. However, trypsin-like proteases could possibly hydrolyze the arg74-gly75 bond of ubiquitin thereby producing a gly-gly-extension peptide and ubiquitin74. The latter is difficult to distinguish from intact ubiquitin on SDS-PAGE gels. Therefore, in order to verify that cleavage of the ubiquitin peptide occurred at the gly76-met1 junction producing the extension peptides, several assays were performed. Since conjugate formation requires the full 76 residue length of the ubiquitin molecule, the generation of conjugates formed by processed ubiquitin was compared with conjugates produced from commercial bovine ubiquitin. The results showed that HeLa conjugates were readily synthesized from each source of ubiquitin thereby proving that the ubiquitin obtained from cleavage of the Ub-carboxyl terminal extended peptide contained the terminal gly76.

The sequence and amino acid composition of each cleaved peptide were also determined as follows. The cleaved peptides were acidified to pH 2, loaded onto a C-18 reverse phase HPLC column and eluted with 0–60% acetonitrile gradient in 0.1 trifluoroacetic acid. The amino acid composition of each peak from HPLC was analyzed with a Beckman 120C analyzer using a w-1 column. Amino acid sequences were determined on an Applied Biosystem 475A sequenator. The direct sequencing of each peptide 1–4 generated the expected order of amino acids. Methionine was shown to be the only N-terminal amino acid present and glycine was not detected on any cycle thereby providing evidence that cleavage occurred at the junction between ubiquitin-gly76 and met1 of the peptide. Acid hydrolysis of each peptide followed by determination of the amino acid compositions of each provided expected results and verified that each purified peptide was full length. A comparison of expected (Exp.) and observed (Obs.) amino acid content of each carboxyl terminal extended peptide (CTEP) is given in the following table:

| Amino Acid | CTEP1 | | CTEP2 | | CTEP3 | | CTEP4 | |
| --- | --- | --- | --- | --- | --- | --- | --- | --- |
| | Exp. | Obs. | Exp. | Obs. | Exp. | Obs. | Exp. | Obs. |
| SER | 4 | 3.5 | 3 | 2.9 | 4 | 3.8 | 3 | 2.9 |
| GLU | 8 | 7.8 | 2 | 2.0 | 3 | 3.1 | 7 | 6.8 |
| PRO | 3 | 2.8 | — | — | 3 | 2.8 | — | — |
| MET | 2 | 2.0 | 2 | 1.9 | 2 | 2.2 | 2 | 2.1 |
| ILE | 1 | 1.1 | — | — | 1 | 1.1 | — | — |
| PHE | 1 | 1.0 | 1 | 1.0 | 1 | 1.0 | 1 | 1.0 |
| HIS | 2 | 2.3 | 2 | 1.8 | 2 | 2.0 | 2 | 1.9 |

Rogers et al, Science 234, 364–368 (1986) proposed that polypeptide chains rich in PEST amino acids, i.e. proline (P), glutamic acid (E), serine (S) and threonine (T) target proteins containing them for rapid intracellular degradation. The four carboxyl terminal extended peptides CTEP1–4, were chosen with the aim of testing the PEST hypothesis which does not form part of the present invention. However, in order to show that other peptides may also be synthesized by the same procedure a 13 residue peptide, Conotoxin GI, rich in cysteine was prepared as a ubiquitin-carboxyl terminal extended peptide. This peptide has the sequence ECCN-PACGRHYSC wherein E is glutamic acid, C is cysteine, N is asparagine, P is proline, A is alanine, G is glycine, R is arginine, H is histidine, Y is tyrosine and S is serine, and it was shown to be correctly synthesized in E. coli.

Polyacrylamide Gel Electrophoresis (PAGE)

The proteins and peptides described in this specification were separated in 8–25% gradient polyacrylamide gels by the method of Laemmli disclosed in Nature 227, 680–685 (1970), with the exception that the Tris concentrations were increased in the separating gel (0.75M) and running buffer (50 mM) to improve resolution of the small peptides prepared according to this invention. The sample buffer contained 100 mM Tris HCl, pH 6.8, 3% SDS, 5% 2-mercaptoethanol, 10% glycerol and 0.02% bromophenol blue. Autoradiograms were obtained by direct exposure of the gel to Kodak XAR x-ray film.

From the above description, it is evident that the present invention can be utilized to prepare a wide variety of peptides as ubiquitin extensions cloned in E. coli or other appropriate procaryotes. The ubiquitin peptide fusion products can be readily processed and the cleavage enzyme does not discriminate against any N-terminal amino acid of the peptide with the exception that proline may be the most difficult. However, the lack of enzyme specificity means that virtually any peptide containing from two up to about forty amino acid residues can be synthesized by the present invention. An additional advantage of the present invention is that the ubiquitin-carboxyl terminal extended peptides may be isolated and purified without cleavage of the peptide. Such products may be useful as such. For example, it may be possible to obtain anti-peptide antibodies by immunizing with ubiquitin-carboxyl terminal extended peptides directly cross-linked to a suitable carrier protein. Any anti-ubiquitin antibodies generated could subsequently be removed, such as on ubiquitin-sepharose columns. One might also use ubiquitin-carboxyl terminal extended peptides directly as ligands for receptors or as substrates for enzymes. Even structural studies on peptide extensions may be possible using uncleaved ubiquitin-carboxyl terminal extended peptides since ubiquitin is very soluble and has been well-characterized by X-ray diffraction and 2D-NMR.

Therefore the present invention is limited in scope only by the appended claims and their functional equivalents.

We claim:

1. A method for synthesis and recovery of a ubiquitin-carboxy terminal extension peptide wherein the peptide contains from about two amino acid residues to forty amino acid residues and wherein the N-terminal amino acid of the peptide is any amino acid except proline, the method comprising the steps of:

(a) cloning a synthetic oligonucleotide encoding the desired peptide to be prepared as an extension of a ubiquitin gene at an appropriate site in a plasmid to form a DNA segment encoding a ubiquitin-carboxyl terminal extension peptide;

(b) transforming said plasmid into an appropriate bacterial expression strain and inducing expression of the ubiquitin-carboxyl terminal extension peptide; and (c) recovering the protein from the cells of said bacteria and separating the ubiquitin-carboxyl terminal extension peptide from the recovered protein.

2. A method according to claim 1 wherein said peptide is made up of between about five and forty amino acid residues.

3. A method according to claim 2 wherein said bacterial expression strain is *E. coli*.

4. A method according to claim 3 wherein the *E. coli* contains a temperature sensitive repressor and expression of the ubiquitin-carboxyl terminal extended peptides is induced by a shift in temperature.

5. A method according to claim 3 wherein the ubiquitin-carboxyl terminal extended peptide is separated from other proteins by means of chromatography.

* * * * *